United States Patent [19]

Borglum

[11] 4,212,943
[45] Jul. 15, 1980

[54] PRODUCTION OF BACTERIAL CELL AGGREGATE

[75] Inventor: Gerald B. Borglum, Elkhart, Ind.

[73] Assignee: Miles Laboratories, Inc., Elkhart, Ind.

[21] Appl. No.: 890,500

[22] Filed: Mar. 27, 1978

[51] Int. Cl.$^2$ ............................ C12K 1/00; C12K 1/08
[52] U.S. Cl. ......................................... 435/180; 435/94
[58] Field of Search ................... 195/31 F, 54, 59, 63, 195/68, 116; 210/54; 435/94, 174, 180, 182

[56] References Cited

U.S. PATENT DOCUMENTS

| | | | |
|---|---|---|---|
| 3,625,828 | 12/1971 | Brownewell | 195/31 F |
| 3,779,869 | 12/1973 | Zienty | 195/68 |
| 3,821,086 | 6/1974 | Lee et al. | 195/31 F X |
| 3,915,904 | 10/1975 | Tonkyn et al. | 210/54 C X |
| 3,935,069 | 1/1976 | Long | 195/31 F |

Primary Examiner—David M. Naff
Attorney, Agent, or Firm—Louis E. Davidson

[57] ABSTRACT

A bacterial cell aggregate having increased particle hardness is produced by contacting a mass of bacterial cells with a cross-linking reaction product of (1) glutaraldehyde, cyanuric halide or combinations thereof and (2) a specific cationic polymer obtained by polymerization of an epihalohydrin and an alkylene polyamine, recovering the resulting aggregate and drying the aggregate.

20 Claims, No Drawings

PRODUCTION OF BACTERIAL CELL AGGREGATE

BACKGROUND AND PRIOR ART

Glucose isomerase is an enzyme that can be employed to catalyze the conversion of glucose (dextrose) to fructose (levulose). It is known that glucose isomerase can be produced by fermentation of certain organisms, such as *Streptomyces flavovirens, Streptomyces echinatur, Streptomyces achromogenus, Streptomyces albus, Streptomyces olivaceus, Bacillus coagulans* and the like, in appropriate nutrient media. The glucose isomerase is formed inside the bacterial cells which grow during its production. The cells can be filtered off from the fermentation beer and used directly as a source of glucose isomerase. Direct commercial use of such enzyme-containing bacterial cells had been hampered, however, by a major disadvantage. The enzyme activity was lost from the cells during use and thus the useful life of the cells was reduced. This disadvantage was overcome by the treatment of the bacterial cells with glutaraldehyde as described in U.S. Pat. No. 3,779,869. Additional techniques for immobilizing the enzyme activity in bacterial cells as well as for forming aggregates of such enzyme-containing bacterial cells are described for example, in U.S. Pat. No. 3,821,086 and its U.S. Pat. Re. Nos. 29,130 and 29,136 and in South African Pat. No. 73/5917. The above U.S. patents relate to use of certain anionic and cationic polyelectrolyte flocculating agents. The South African patent discloses various combinations of binders, reinforcing agents and cross-linking agents. While the above techniques provided bacterial cell aggregates which generally retained their enzyme activity during use, there was still a need to increase the hardness of the aggregates so that they could be commercially used in reactor beds of increasing depth. U.S. Pat. No. 3,935,069 describes the addition of certain metallic compounds in conjunction with polyelectrolyte flocculating agents to improve the hardness. However, this technique has limited utility.

SUMMARY OF THE INVENTION

In accordance with the present invention, a process is provided for the production of an aggregate of bacterial cells having improved hardness. This process involves the use of a cross-linking reaction product of glutaraldehyde and/or cyanuric halide and a particular epihalohydrin-polyamine polymer. In particular, this invention relates to a process for producing an aggregate of bacterial cells which comprises contacting a mass of bacterial cells with a cross-linking reaction product of (1) a material selected from the class consisting of glutaraldehyde, cyanuric halide and combinations thereof and (2) a water-soluble cationic polymer obtained by the polymerization of an epihalohydrin with an alkylene polyamine having the formula $R_1R_2NRNH_2$ wherein R is a lower alkylene having from 2 to about 6 carbon atoms, and $R_1$ and $R_2$ are each a lower alkyl of from 1 to about 6 carbon atoms, the mole ratio of epihalohydrin to polyamine being from about 0.60:1 to about 2.7:1, said polymerization comprising reacting with the alkylene polyamine from about 50 to about 90 percent of the amount of epihalohydrin to be polymerized, allowing the reaction to continue until the reaction medium attains a substantially uniform viscosity, and reacting the remaining portion of the epihalohydrin incrementally to obtain the cationic polymer, the temperature of polymerization being from about 60° C. to about 120° C., and recovering the resulting aggregate. This invention is especially useful when the resulting aggregate is dried and then rehydrated for subsequent use.

DESCRIPTION OF THE INVENTION

The process of the present invention can be used with various enzyme-containing bacterial cells. The remainder of the disclosure will be directed at using the process with bacterial cells containing glucose isomerase activity.

The bacterial cells containing glucose isomerase activity useful in the process of the present invention can be produced by well-known procedures. The preferred enzyme-containing cells are produced by growing under submerged aerobic conditions a culture of *Streptomyces olivaceus* NRRL 3583 or mutants thereof in a medium containing appropriate nutrients. This is described in U.S. Pat. No. 3,625,828. The resulting bacterial cells are separated from the fermentation beer by filtration or centrifugation.

The ingredients employed in this process are readily available. Glutaraldehyde and cyanuric halide, such as cyanuric trichloride, cyanuric tribromide, cyanuric triiodide and the like, are commercially available or can be produced by well-known techniques. The particular epihalohydrin-polyamine polymer used in this process is commercially available under the trademark BETZ 1180 from Betz Laboratories, Inc. Trevose, Penn. BETZ 1180 has a molecular weight less than one million, contains about 0.288 millimoles of amino groups per gram of solution (based on ninhydrin assay) and is marketed as a solution containing 30 weight percent solids, based on total solution weight. This compound is disclosed in U.S. Pat. No. 3,915,904. The compound is described therein as a water-soluble cationic polymer obtained by the polymerization of an epihalohydrin with an alkylene polyamine having the formula $R_1R_2NRNH_2$ wherein R is a lower alkylene having from 2 to about 6 carbon atoms, and $R_1$ and $R_2$ are each a lower alkyl of from about 1 to about 6 carbon atoms, the mole ratio of epihalohydrin to polyamine being from about 0.60:1 to about 2.7:1, said polymerization comprising reacting with the alkylene polyamine from about 50 to about 90 percent of the amount of epihalohydrin to be polymerized, allowing the reaction to continue until the reaction medium attains a substantially uniform viscosity, and reacting the remaining portion of the epihalohydrin incrementally to obtain the cationic polymer, the temperature of polymerization being from about 60° C. to about 120° C. This material will hereinafter be referred to as the "polyamine polymer".

The cross-linking reaction product employed in the present invention to form the bacterial cell aggregate can be one of three possible compositions. The polyamine polymer can be reacted with glutaraldehyde or cyanuric halide or with both glutaraldehyde and cyanuric halide.

The glutaraldehyde and/or cyanuric halide, which is collectively identified as component (1), is reacted with the polyamine polymer, which is identified as component (2), at a pH about 6 to 10 and at about 0° to 30° C. for about 0.5 to 2.5 hours. The overall cross-linking reaction product contains from about 12 to about 77 weight percent of component (1) and from about 23 to about 88 weight percent of component (2) based on the total weight of the active ingredients in components (1)

and (2). The glutaraldehyde content of the reaction product is from about 0 to about 77 weight percent and the cyanuric halide content is from about 0 to about 22 weight percent based on the total weight of the active ingredients in components (1) and (2).

The reaction between glutaraldehyde and the polyamine polymer is preferably carried out at pH 8 to 9 and at about 18° to 25° C. for about 0.5 hour. The glutaraldehyde should be present in a molar ratio of at least one mole per mole of amino group in the polyamine polymer in order to avoid undesirable cross-linking of the polyamine polymer with glutaraldehyde.

The reaction between cyanuric halide alone and the polyamine polymer is preferably carried out at pH 8 to 9 and at 0° to 10° C. for about 1 to 2 hours. The cyanuric halide should be present in a molar ratio of at least one mole per mole of amino group in the polyamine polymer in order to avoid undesirable cross-linking of the polyamine polymer with cyanuric halide. Cyanuric halide, such as cyanuric trichloride, has three halogen reactive sites. One of these sites will react at 0° C. or higher. After reaction at the first site, the second site will react at 30° to 50° C. and the final site will react at 90° to 100° C. It is desirable to initially react only the first site on the cyanuric halide with the polyamine polymer. When the resulting cross-linking reaction product is subsequently reacted with the bacterial cells and heated to higher temperatures during drying, the remaining reactive sites on the cyanuric halide will then react with the polyamine polymer to provide additional cross-linking to the bacterial cell aggregate.

The reaction between the polyamine polymer and the combination of glutaraldehyde and cyanuric halide is carried out in steps. First, the cyanuric halide is reacted with the polyamine polymer at pH 8 to 9 and at 0° to 10° C. for about 1 to 2 hours. Preferably, in this situation the reactants have a mole ratio of one mole of cyanuric halide to two moles of amino groups on the polyamine polymer. An excess amount of glutaraldehyde is then added and the reaction is continued under the same pH and temperature conditions for about 0.5 hour.

The cross-linking reaction product employed in the present invention is not a cationic polyelectrolyte, since the amino groups on the polyamine polymer which initially provided the cationic characteristic have been reacted with the glutaraldehyde and/or cyanuric halide and are thus no longer available.

Bacterial cell aggregates are prepared by contacting a mass of bacterial cells with the cross-linking reaction product prepared as described above at pH about 8 to 9 and at about 0° to 30° C. for about 0.5 to 1.5 hours. The cross-linking reaction product is employed in such amount and concentration that the bacterial cells are contacted with from about 4.5 to about 60 weight percent of the cross-linking reaction product active ingredients based upon the dry weight of the cells.

After the above reaction takes place, the resulting bacterial cell aggregate is preferably extruded or otherwise formed into desirable shapes and then dried at about 65° C. for several hours. The resulting dried aggregate can be stored until subsequently needed for use in an enzymatic process. At that time the dried aggregate is rehydrated and conditioned for use. One illustrative conditioning process is described in U.S. Pat. No. 3,974,036.

A principal advantage of the present invention is an increase in the hardness of the bacterial cell aggregate after rehydration as compared to prior art bacterial cell aggregates. The hardness is expressed in relation to resistance to compression of the bacterial cell aggregate particles. An Instron Tensile Tester using a Compression Load Cell No. CCT was employed in a manner similar to that described in U.S. Pat. No. 3,935,069. This instrument is available from Instron Corporation, Canton, Mass.

The following is the Rehydration Hardness Assay Procedure:

A rehydration solution is prepared by mixing 9.68 g $CoCl_2.6H_2O$, 28.0 g $Mg(OH)_2$ and 56.0 g anhydrous citric acid in 600 ml. distilled water at 45° C. The mixture is stirred and heated to 60° C. to dissolve all the salts. It is then cooled to 25° C. and adjusted to pH 8.5 with NaOH. It is then filtered and brought to 1.0 l. volume with distilled water. A 2.5 ml. portion of the above solution is mixed with 130 ml. water, 70.3 g dextrose, 24.228 g tris (hydroxymethyl) aminomethane and adjusted to pH 8.55 at 25° C. with NaOH. It is then brought to 200 ml. with distilled water.

Five particles of dried bacterial cell aggregate are covered with 2.5 ml. of the above rehydration solution in a petri dish and heated at 60° C. in a water bath for one hour and then allowed to stand at room temperature until cooled. The particles are removed from the solution, excess surface liquid is removed, and then they are tested on the Instron instrument. The instrument is warmed up for at least 30 minutes with the load cell attached before being used for measurements. Set crosshead speed at 0.2 in/min. (5.1 mm./min.) and the chart speed at 2.0 in./min. (51 mm./min.). Set the "Return" to halt at 0.038 in. (0.965 mm.) for the surface of the load cell. Set "Gage Length" to clear the lip of the sample cup. Set the recorder to full scale range. This is usually 10 pounds (4.54 kg.). Standardize the recorder to read zero pounds (or zero kg.) with the sample cup on the load cell and one pound (0.454 kg.) with the cup and one pound (0.454 kg.) standard weight on the load cell. Place a single rehydrated particle on the sample cup centered with the crosshead. Manually lower the crosshead to the top of the particle and press the "Run" button. On the recorder read the force in pounds (kg.) at a distance of 0.03 in. (0.762 mm.) from the point at which the cross-head touches the particle. The hardness is thus expressed in the force (pounds of kilograms) needed to compress the particle 0.03 in. (0.762 mm.). The test is repeated for several particles and the results are averaged.

The invention is described in further detail in the following illustrative examples.

EXAMPLE 1

A cross-linking reaction product was obtained by adding 2.25 g. BETZ 1180 solution containing 0.675 g. active material and 0.648 millimoles amino groups to 100 ml. of 1.25 percent (weight/volume basis) glutaraldehyde containing 13.24 millimoles active material at pH 9. The mixture was stirred for about 30 minutes and became a deep yellow solution. The resulting product was formed from a reaction mixture containing 64.9 weight percent glutaraldehyde and 35.1 weight percent polyamine polymer based on total weight of the glutaraldehyde (Component 1) and the polyamine polymer (Component 2).

A culture of a mutant of *Streptomyces olivaceus* NRRL 3583 was grown in an agitated aerated fermentor containing an appropriate nutrient medium described in U.S. Pat. No. 3,625,828. The resulting fermentor broth containing a mass of bacterial cells was adjusted to pH 8.2 by addition of appropriate buffering materials. A portion of the above-prepared solution was added to a portion of the fermentor broth in an amount to provide the equivalent of 14 weight percent glutaraldehyde (21.6 weight percent total reaction product) based on the dry weight of the bacterial cells. After 30 minutes reaction time at 25° C. and pH 8.2, the treated broth was filtered. The filter cake was then extruded through a syringe opening of 2.2 mm. The resulting extruded strands were cut into individual 30 mm. lengths and dried overnight at 65° C. in a forced warm air oven. A similar portion of fermentor broth was treated with glutaraldehyde alone at a concentration of 14 weight percent based on bacterial cell dry weight. The treated cells were then filtered, extruded and dried in the same manner to produce Control particles. Both the Control and the cross-linking reaction product treated materials were tested for hardness. The Control sample had a hardness of 0.8 lb. (0.364 kg.) while the product prepared in accordance with the present invention had the improved hardness of 2.8 lb. (1.27 kg.).

EXAMPLE 2

Portions of *Streptomyces olivaceus* fermentor broth similar to that of Example 1 were treated with glutaraldehyde alone (Control) and with various combinations of cross-linking reaction products at pH 9 and 29° C. The various cross-linking reaction products were prepared as described in Example 1 above using various amounts of glutaraldehyde and polyamine polymer. The treated bacterial cells were then filtered, extruded, dried and tested for hardness. The results are shown in the following Table I.

TABLE I

| Reaction Mixture for Composition of Cross-Linking Reaction Product (weight percent) | | Amount Added | |
|---|---|---|---|
| Glutaraldehyde | Polyamine Polymer | (Weight Percent) | Hardness lb. (kg.) |
| 100 (Control) | | 13.9 | 1.8 (0.82) |
| 76.7 | 23.3 | 13 | 2.7 (1.23) |
| 40.0 | 60.0 | 34.7 | 2.7 (1.23) |
| 44.4 | 55.6 | 18.7 | 3.3 (1.5) |
| 65.1 | 34.9 | 29.8 | 3.6 (1.64) |

It can be seen that the use of the cross-linking reaction product enables consistently increased hardness to be obtained as compared to the prior art use of glutaraldehyde alone.

EXAMPLE 3

A cross-linking reaction product was obtained by dissolving 0.188 g cyanuric trichloride (0.64 millimoles) in 10 ml. acetone and then adding this solution with stirring to 70 ml. ice-cold water to give a finely-divided precipitate. A 2.25 g portion of BETZ 1180 solution (containing 0.675 g active material and 0.648 millimoles amino groups) was diluted with 20 ml. water and added to the cyanuric trichloride suspension. The resulting mixture was stirred and maintained at pH 9 and 0°–5° C. for 1–2 hours, then diluted to 100 ml. The cyanuric trichloride dissolved indicating reaction with the polyamine. This reaction product resulted from a reaction mixture containing 21.8 weight percent cyanuric trichloride as component (1) and 78.2 weight percent polyamine polymer as component (2). A portion of a *Streptomyces olivaceus* fermentor broth similar to that of Example 1 was mixed with a portion of the above reaction product to provide a concentration of 32.0 weight percent reaction product based on dry weight of the bacterial cells. A 0.2 percent (weight/volume basis) aqueous sodium bicarbonate solution was added to maintain pH at 9. After 1.5 hours at pH 9 and 25° C. the treated broth was filtered, extruded and dried as described in Example 1. Another portion of fermentor broth was treated as above for 0.5 hour. No sodium bicarbonate was initially added, but the filtered cells were washed with 1 weight percent sodium bicarbonate solution at pH 9 before extruding and drying. For a Control, glutaraldehyde was added to a separate portion of the fermentor broth at a concentration of 14 weight percent based on the dry weight of the bacterial cells. The cells were treated with glutaraldehyde for 30 minutes at pH 8.2 and 25° C. before filtering, extruding and drying. The Control produced a hardness of 2.2 lb. (1 kg.) while the 0.5 hour reaction product treatment produced a hardness of 3.8 lb (1.73 kg.) and the 1.5 hours reaction product treatment produced a hardness of 4.0 lb (1.82 kg.).

EXAMPLE 4

A cross-linking reaction product was obtained by adding 4.5 g BETZ 1180 solution (containing 1.35 g active material and 1.296 millimoles of amino groups) to 0.118 g (0.64 millimoles) of finely-divided cyanuric trichloride in ice-cold water. The pH was adjusted to 9 and was maintained at pH 9 in an ice-bath (0° C.) for two hours. Then 1.25 g (13.24 millimoles) of glutaraldehyde at pH 9 was added and the low temperature maintained for about 0.5 hour. A dark yellow color developed. The reaction product resulted from a reaction mixture containing 4.3 weight percent cyanuric trichloride, 46.0 weight percent glutaraldehyde (total of 50.3 weight percent component 1) and 49.7 weight percent polyamine polymer as component (2). A portion of a *Streptomyces olivaceus* fermentor broth similar to that of Example 1 was mixed with a portion of the above reaction product to provide a concentration of 30.4 weight percent reaction product based on dry weight of the bacterial cells. After a 0.5 hour reaction period at pH 9 and 25° C. the treated broth was filtered, washed with 5 weight percent aqueous sodium bicarbonate solution at pH 9, extruded and dried. A Control sample was prepared in the manner described in Example 3. The Control produced a hardness of 0.8 lb. (0.364 kg.) while the cross-linking reaction product produced a hardness of 3.8 lb. (1.73 kg.).

EXAMPLE 5

Portions of *Streptomyces olivaceus* fermentor broth similar to that of Example 1 were treated with glutaraldehyde alone (Control) and with various combinations of reaction products at pH 9 and at 25° C. and 5° C. The cross-linking reaction products all employed one mole of cyanuric trichloride per two moles of amino groups in the polyamine polymer. The overall amounts of glutaraldehyde and polyamine polymer were then adjusted to produce the combinations set forth in Table II below. The treated bacterial cells were then filtered, extruded, dried and tested for hardness. The results are shown in the following Table II.

TABLE II

Composition of Reaction Mixture for Cross-Linking Reaction Product (weight percent)

| Glutaraldehyde | Cyanuric Trichloride | Polyamine Polymer | Amount Added (weight percent) | Hardness lb. (kg.) |
|---|---|---|---|---|
| 25° C. | | | | |
| 100 (Control) | — | — | 7 | 1.2 (0.55) |
| 30.6 | 5.1 | 64.3 | 6.5 | 2.3 (1.05) |
| 18.2 | 6.0 | 75.8 | 38.4 | 2.1 (0.96) |
| 47.4 | 3.8 | 48.8 | 29.5 | 3.1 (1.41) |
| — | 12.8 | 87.2 | 55.0 | 3.3 (1.50) |
| 5° C. | | | | |
| 100 (Control) | — | — | 7 | 1.2 (0.55) |
| 52.0 | 3.5 | 44.5 | 13.5 | 4.4 (2.0) |
| 18.8 | 5.9 | 75.3 | 15.9 | 5.7 (2.6) |

It should be noted that in all the above examples the bacterial cells treated with the cross-linking reaction products all had significantly increased hardness values as compared to the bacterial cells treated with the prior art glutaraldehyde alone.

When a cross-linking reaction product produced from glutaraldehyde and polyamine polymer is used, the preferred composition is produced from a mixture of 57.1 weight percent glutaraldehyde as component (1) and 42.9 weight percent polyamine polymer as component (2) based on the total weight of the active ingredients in components (1) and (2). This composition is also preferably employed in an amount of 17.5 weight percent based on the dry weight of the bacterial cells.

When a cross-linking reaction product produced from glutaraldehyde, cyanuric trichloride and polyamine polymer is used, the preferred composition is produced from a mixture of 54.9 weight percent glutaraldehyde and 3.6 weight percent cyanuric trichloride as component (1) and 41.5 weight percent of polyamine polymer as component (2) based on the total weight of the active ingredients in components (1) and (2). This composition is also preferably employed in an amount of 18.2 weight percent based on the dry weight of the bacterial cells.

The bacterial aggregates produced in the manner described above were all capable of converting glucose to fructose. The glucose isomerase activity was not impaired through the use of this novel process.

What is claimed is:

1. A process for producing an aggregate of *Streptomyces olivaceus* bacterial cells which comprises contacting a mass of *Streptomyces olivaceus* bacterial cells with a cross-linking reaction product of (1) a material selected from the class consisting of glutaraldehyde, cyanuric halide and combinations thereof and (2) a water-soluble cationic polymer obtained by the polymerization of an epihalohydrin with an alkylene polyamine having the formula $R_1R_2NRNH_2$ wherein R is a lower alkylene having from 2 to about 6 carbon atoms, and $R_1$ and $R_2$ are each a lower alkyl of from 1 to about 6 carbon atoms, the mole ratio of epihalohydrin to polyamine being from about 0.60:1 to about 2.7:1, said polymerization comprising reacting with the alkylene polyamine from about 50 to about 90 percent of the amount of epihalohydrin to be polymerized, allowing the reaction to continue until the reaction medium attains a substantially uniform viscosity, and reacting the remaining portion of the epihalohydrin incrementally to obtain the cationic polymer, the temperature of polymerization being from about 60° C. to about 120° C., and recovering the resulting aggregate.

2. A process according to claim 1 wherein component (1) of the cross-linking reaction product is glutaraldehyde.

3. A process according to claim 1 wherein component (1) of the cross-linking reaction product is cyanuric halide.

4. A process according to claim 1, wherein component (1) of the cross-linking reaction product is a combination of glutaraldehyde and cyanuric halide.

5. A process according to claim 1 wherein the bacterial cells are contacted with the cross-linking reaction product at pH about 8 to 9 and at about 0° to 30° C. for about 0.5 to 1.5 hours.

6. A process according to claim 1 wherein the bacterial cells are contacted with from about 4.5 to about 60 weight percent of the cross-linking reaction product based upon the dry weight of the cells.

7. A process according to Claim 1 wherein the cross-linking product results from the reaction of from about 12 to about 77 weight percent of component (1) and from about 23 to about 88 weight percent of component (2) based on the total weight of the active ingredients in components (1) and (2).

8. A process according to claim 7 wherein component (1) of the cross-linking reaction product contains from about 0 to about 77 weight percent glutaraldehyde and from about 0 to about 22 weight percent cyanuric halide and wherein the total amount of glutaraldehyde and/or cyanuric halide is from about 12 to about 77 weight percent, said weight percents based on the total weight of the active ingredients in components (1) and (2).

9. A process according to claim 1 wherein the cyanuric halide is cyanuric trichloride.

10. A process according to claim 1 wherein the cross-linking product results from the reaction of 57.1 weight percent glutaraldehyde as component (1) and 42.9 weight percent of component (2), based on the total weight of the active ingredients in components (1) and (2), and such cross-linking reaction product is used in an amount of 17.5 weight percent based on the dry weight of the bacterial cells.

11. A process according to claim 1 wherein the cross-linking product results from the reaction of 54.9 weight percent glutaraldehyde and 3.6 weight percent cyanuric trichloride as component (1) and 41.5 weight percent of component (2), based on the total weight of the active ingredients in components (1) and (2), and such cross-linking reaction product is used in an amount of 18.2 weight percent based on the dry weight of the bacterial cells.

12. A process according to claim 1 wherein the cross-linking reaction product is obtained by reacting components (1) and (2) at a pH about 6 to 10 and about 0° to 30° C. for about 0.5 to 2.5 hours.

13. A process according to claim 1 wherein the recovered aggregate is then dried.

14. An aggregate of bacterial cells produced by the process of claim 1.

15. A process for producing an aggregate of *Streptomyces olivaceus* bacterial cells which comprises contacting a mass of such bacterial cells at pH about 8 to 9 and at about 0° to 30° C. for about 0.5 to 1.5 hours with from about 4.5 to about 60 weight percent, based on the dry weight of such cells, of a cross-linking product resulting from the reaction of (1) from about 12 to about 77 weight percent of a material selected from the class consisting of glutaraldehyde, cyanuric trichloride and combinations thereof and (2) from about 23 to about 88 weight percent of a water-soluble cationic polymer obtained by the polymerization of an epihalohydrin with an alkylene polyamine having the formula $R_1R_2NRH_2$ wherein R is a lower alkylene having from 2 to about 6 carbon atoms, and $R_1$ and $R_2$ are each a lower alkyl of from 1 to about 6 carbon atoms, the mole ratio of epihalohydrin to polyamine being from about 0.60:1 to about 2.7:1, said polymerization comprising reacting with the alkylene polyamine from about 50 to about 90 percent of the amount of epihalohydrin to be polymerized, allowing the reaction to continue until the reaction medium attains a substantially uniform viscosity, and reacting the remaining portion of the epihalohydrin incrementally to obtain the cationic polymer, the temperature of polymerization being from about 60° C. to about 120° C., said weight percents of components (1) and (2) being based on the total weight of the active ingredients in components (1) and (2), said reaction between components (1) and (2) taking place at a pH about 6 to 10 and about 0° to 30° C. for about 0.5 to 2.5 hours, and recovering the resulting aggregate.

16. A process according to claim 15 wherein component (1) of the cross-linking reaction product is glutaraldehyde.

17. A process according to claim 15 wherein component (1) of the cross-linking reaction product is a combination of glutaraldehyde and cyanuric trichloride.

18. A process according to claim 15 wherein the cross-linking product results from the reaction of 57.1 weight percent glutaraldehyde as component (1) and 42.9 weight percent of component (2), based on the total weight of the active ingredients in components (1) and (2), and such cross-linking reaction product is used in an amount of 17.5 weight percent based on the dry weight of the bacterial cells.

19. A process according to claim 15 wherein the cross-linking product results from the reaction of 54.9 weight percent glutaraldehyde and 3.6 weight percent cyanuric trichloride as component (1) and 41.5 weight percent of component (2), based on the total weight of the active ingredients in components (1) and (2), and such cross-linking reaction product is used in an amount of 18.2 weight percent based on the dry weight of the bacterial cells.

20. A process according to claim 15 wherein the recovered aggregate is then dried.

* * * * *